United States Patent
Ezoe et al.

(10) Patent No.: US 9,314,211 B2
(45) Date of Patent: Apr. 19, 2016

(54) BLOOD PRESSURE MEASUREMENT DEVICE HAVING FUNCTION OF DETERMINING REST CONDITION OF PATIENT

(71) Applicant: OMRON HEALTHCARE Co., Ltd., Kyoto (JP)

(72) Inventors: Mika Ezoe, Osaka (JP); Yukiya Sawanoi, Nara (JP); Shingo Yamashita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 250 days.

(21) Appl. No.: 13/955,390

(22) Filed: Jul. 31, 2013

(65) Prior Publication Data

US 2015/0038802 A1 Feb. 5, 2015

(51) Int. Cl.
*A61B 5/09* (2006.01)
*A61B 5/024* (2006.01)
*A61B 5/022* (2006.01)
*A61B 5/00* (2006.01)

(52) U.S. Cl.
CPC ............ *A61B 5/7282* (2013.01); *A61B 5/022* (2013.01); *A61B 5/024* (2013.01); *A61B 5/742* (2013.01)

(58) Field of Classification Search
CPC ........ A61B 5/022; A61B 5/024; A61B 5/742; A61B 5/7282; A61B 18/22; A61B 18/2277; G02B 6/262; G02B 6/0283; G02B 6/06327
USPC ......... 600/300, 301, 481, 483–485, 500, 501, 600/509, 513
See application file for complete search history.

(56) References Cited

U.S. PATENT DOCUMENTS

| | | | |
|---|---|---|---|
| 2005/0187480 A1* | 8/2005 | Kario et al. | 600/483 |
| 2007/0232939 A1* | 10/2007 | Forstner | 600/495 |
| 2011/0224560 A1* | 9/2011 | Kitamura et al. | 600/493 |

FOREIGN PATENT DOCUMENTS

JP 2012-120206 A 6/2012

* cited by examiner

*Primary Examiner* — Gary Jackson
*Assistant Examiner* — Boniface N Nganga
(74) *Attorney, Agent, or Firm* — Osha Liang LLP

(57) ABSTRACT

A method includes pressurizing a cuff of a blood pressure measurement device that is wrapped around a measurement site of a patient, measuring the patient's blood pressure and pulse period during and before depressurization of the cuff, calculating a threshold value range of the pulse period based on data of a past measured pulse period of the patient, determining whether the measured pulse period is within the threshold value range of the past measured pulse period, if the measured pulse period is determined to be within the threshold value range of the past measured pulse period both during and before depressurization, displaying that the patient was in the rest condition, and if the measured pulse period is determined not to be within the threshold value range of the past measured pulse period either during or before depressurization, displaying that the patient was in the unrest condition.

10 Claims, 7 Drawing Sheets

| | Time Lapse | Pulse Period |
|---|---:|---:|
| Pressurization Phase | 0.725 | 0.754167 |
| | 1.479167 | 0.75 |
| | 2.229167 | 0.741667 |
| | 2.970833 | 0.745833 |
| | 3.716667 | 0.754167 |
| | 4.475 | 0.754167 |
| | 5.229167 | 0.754167 |
| | 5.983333 | 0.75 |
| | 6.733333 | 0.758333 |
| | 7.491667 | 0.745833 |
| Depressurization Phase | 8.2375 | 0.75 |
| | 8.9875 | 0.754167 |
| | 9.741667 | 0.754167 |
| | 10.49583 | 0.758333 |
| | 11.25417 | 0.758333 |
| | 12.0125 | 0.7625 |
| | 12.775 | 0.754167 |
| | 13.52917 | 0.7625 |
| | 14.29167 | 0.758333 |
| | 15.05 | 0.766667 |
| | 15.81667 | 0.7625 |
| | 16.57917 | 0.7625 |
| | 17.34167 | 0.7625 |
| | 18.10417 | 0.758333 |
| | 18.8625 | 0.7625 |
| | 19.625 | 0.754167 |
| | 20.37917 | 0.75 |
| | 21.12917 | 0.754167 |
| | 21.88333 | 0.75 |
| | 22.63333 | 0.754167 |
| | 23.3875 | 0.754167 |
| | 24.14167 | 0.75 |
| | 24.89167 | 0 |

*FIG. 4B*

BLOOD PRESSURE MEASUREMENT DEVICE HAVING FUNCTION OF DETERMINING REST CONDITION OF PATIENT

BACKGROUND (1) Field of the Invention

The present invention relates to a blood pressure measurement device and methods for measuring blood pressure. More specifically, the present invention relates to apparatus and methods for determining whether a patient was in a rest condition during blood pressure measurement.

(2) Description of Related Art

A rest condition of a patient is important when measuring blood pressure. If the patient is not in a rest condition, the measured blood pressure may differ from the value measured in the rest condition. Thus, it is necessary to know whether the patient was in the rest condition when the blood pressure was being measured.

As a measure to determine whether a patient was in a rest condition, measuring pulse rate and pulse wave period is known. Generally, the patient's pulse wave period becomes short or unstable after hard exercise or mental distress. Therefore, it is possible to determine whether the patient was in the rest condition by examining whether the patient's pulse wave period was stable during a certain period of time.

Rossmax Hemodynamic Stability Determination (HSD) discloses that when a patient is not in a rest condition due to mental or physical load, his or her pulse period may become short and/or unstable, which may cause blood pressure measurement error.

JPH2012-120206 discloses the relationship between an increase of pulse rate and pulse period change at the time when a patient received stress.

However, because most blood pressure devices require use of a cuff to be mounted on an arm of the patient, some patients may feel stress during blood pressure measurement. In that event, the pulse period of the patient may be significantly affected by the stress that was caused by the cuff. Therefore, even if the patient was a under rest condition before measurement, the pulse period measured by using the blood pressure measurement device may become different from the pulse period of the patient in the rest condition.

SUMMARY OF INVENTION

Therefore, a blood pressure measurement device or method according to one or more embodiments of the present invention accurately determines whether a patient was in a rest condition during blood pressure measurement while taking into account (or regardless of) a change of the pulse period that may be caused by use of a cuff of the blood pressure measurement device.

According to one or more embodiments of the present invention, during measurement of blood pressure, the pulse period of the patient is measured over a plurality of phases: before, during and after pressurization of the cuff. The pulse periods measured during those phases are each compared with the pulse period of past measurement(s) of corresponding phases.

According to one or more embodiments of the present invention, a comparison of the pulse period may be made in terms of: a time period between pulse waves (pulse rate), a change of time period between the pulse waves (pulse rate variability), or both.

According to one or more embodiments of the present invention, pulse rate in a phase may be calculated by the time period of the phase divided by the number of pulses during the phase. According to one or more embodiments of the present invention, a change of pulse period in a phase may be calculated by the difference between a maximum time period of a pulse and a minimum time period of a pulse during the phase.

According to one or more embodiments of the present invention, a threshold value range for comparing a present measurement with past measurement(s) may be calculated by using a pulse period (time period of a pulse wave and/or change of pulse period) measured in the past measurement(s) of the same patient during the phases.

According to one or more embodiments of the present invention, if the pulse period (time period of a pulse wave and/or change of pulse period) measured in any one of those phases is beyond or below the threshold value range, the patient is determined to have been under an unrest condition at the time of measurement.

According to one or more embodiments of the present invention, a method of determining a rest or an unrest condition of a patient during measurement of blood pressure of the patient includes: providing a cuff of a blood pressure measurement device that is configured to be wrapped around a measurement site of the patient, and pressurizing the cuff; measuring the blood pressure and a pulse period of the patient during and before depressurization of the cuff; calculating a threshold value range of the pulse period measured during and before depressurization of the cuff based on data of a pulse period measured in a past measurement of the patient and stored in a memory of the blood pressure measurement device; determining whether the pulse period of the patient measured during and before depressurization of the cuff is within the threshold value range of the pulse period stored in the memory; if the pulse period measured during and before depressurization is determined to be within the threshold value range of the pulse period stored in the memory both during and before depressurization, displaying on a display of the blood pressure measurement device that the blood pressure was measured when the patient was in the rest condition, and if the pulse period measured during and before depressurization is determined not to be within the threshold value range of the pulse period stored in the memory either during or before depressurization, displaying on the display of the blood pressure measurement device that the blood pressure was measured when the patient was in the unrest condition.

According to one or more embodiments of the present invention, a blood pressure measurement device that determines a rest or an unrest condition of a patient includes: a cuff for mounting on a measurement site of the patient, wherein the cuff is configured to be pressurized and depressurized to measure a blood pressure and a pulse period of the patient; means for measuring the blood pressure and the pulse period of the patient during and before depressurization of the cuff; a memory that stores data of a pulse period measured in a past measurement of the patient by the measuring means; a threshold calculation section that calculates a threshold value of the pulse period measured during and before depressurization of the cuff based on data of the pulse period measured in the past measurement of the patient; a rest/unrest condition determination section that determines whether the patient was in a rest condition or an unrest condition during blood pressure measurement by comparing the pulse period measured during and before depressurization of the cuff with the threshold value based on data of the pulse period measured in the past measurement of the patient; a display unit that displays the measured blood pressure and whether the blood pressure was measured during the rest condition or the unrest condition of the patient.

According to one or more embodiments of the present invention, a blood pressure measurement device that determines a rest or an unrest condition of a patient includes: a cuff for mounting on a measurement site of the patient, wherein the cuff includes an air bladder and is configured to be pressurized and depressurized to measure a blood pressure and a pulse period of the patient; a measurement air system comprising a pressure sensor, a pump, and a valve; an air tube that connects the air bladder of the cuff to the measurement air system; a blood pressure calculation section that calculates a blood pressure of the patient based on an internal pressure of the air bladder as detected by the pressure sensor; a heart rate/pulse period change calculation section that calculates a pulse rate of the patient during and before depressurization of the cuff and a pulse period change of the patient during and before depressurization of the cuff based on the measured pulse period of the patient; a memory that stores data of a pulse period measured in a past measurement of the patient; a threshold calculation section that calculates a threshold value of at least one of the pulse rate of the patient calculated during and before depressurization of the cuff and the pulse period change of the patient calculated during and before depressurization of the cuff based on data of the pulse period measured in the past measurement of the patient; a rest/unrest condition determination section that determines whether the patient was in a rest condition or an unrest condition during blood pressure measurement by comparing at least one of the pulse rate of the patient calculated during and before depressurization of the cuff and the pulse period change of the patient calculated during and before depressurization of the cuff with the threshold value based on data of the pulse period measured in the past measurement of the patient; and a display unit that displays the measured blood pressure and whether the blood pressure was measured during the rest condition or the unrest condition of the patient.

BRIEF DESCRIPTION OF DRAWINGS

FIGS. 4(A) and 4(B) show measurement data of pulse periods during pressurization and depressurization phases of the cuff of the blood pressure measurement device (sphygmomanometer) according to one or more embodiments of the present invention.

DETAILED DESCRIPTION OF INVENTION

Figure 1:
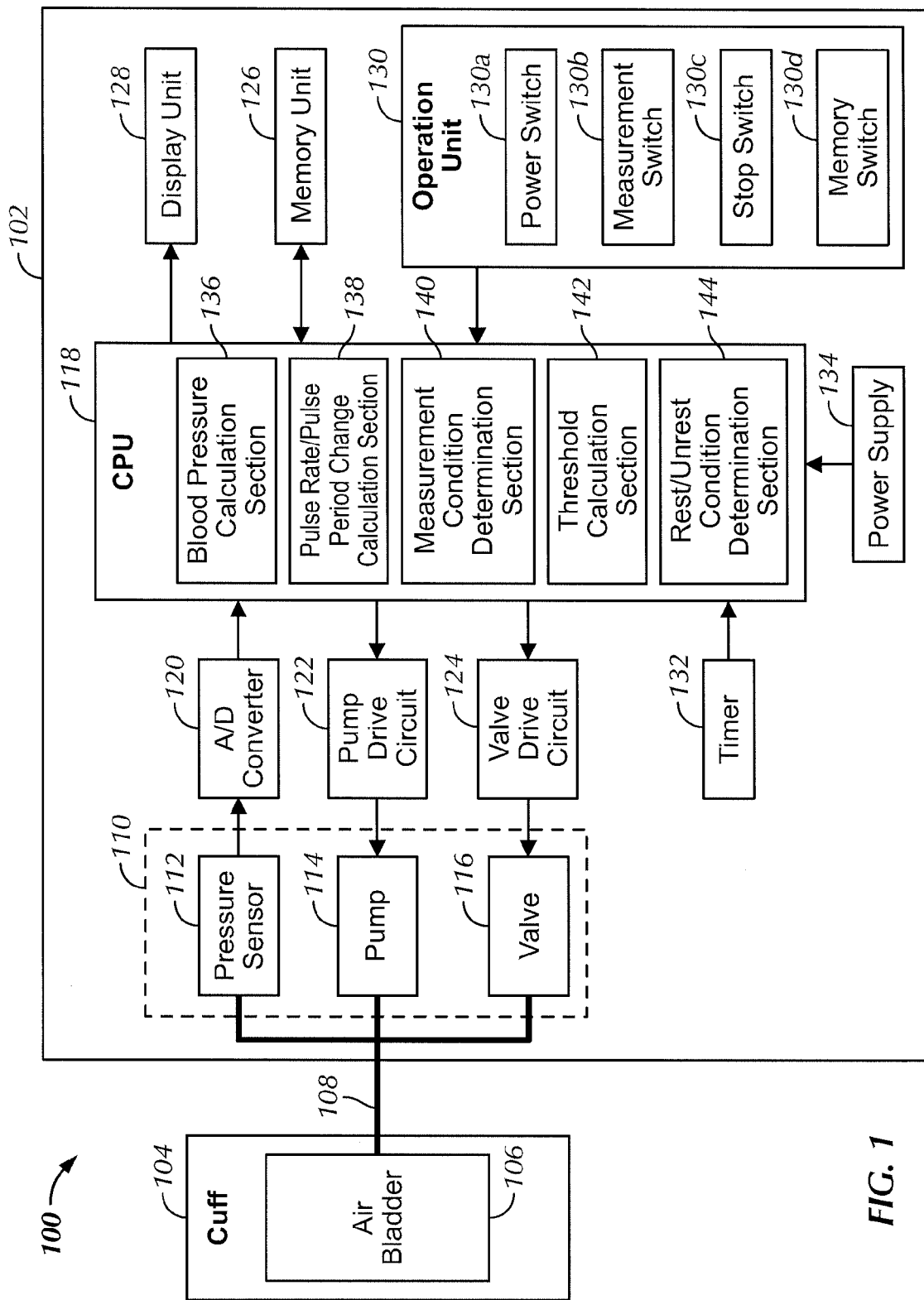
FIG. 1 is a functional block diagram showing a configuration of a blood pressure measurement device (sphygmomanometer) according to one or more embodiments of the present invention.

Hereinafter, embodiments of a blood pressure measurement device according to one or more embodiments of the present invention will be described with reference to the drawings. In the following description, the same reference numerals are given to the same components and constituent elements. The names and functions thereof are also the same.

FIG. 1 is a functional block diagram showing a configuration of a blood pressure measurement device (sphygmomanometer) according to one or more embodiments of the present invention.

Referring to FIG. 1, the blood pressure measurement device (sphygmomanometer) 100 is provided with a device main body 102 and a cuff 104. When blood pressure measurement is performed by the sphygmomanometer 100, the cuff 104, which has a belt-like outer shape, is wrapped around a measurement site of the patient. The cuff 104 houses an air bladder 106 serving as a fluid bag for compressing the measurement site.

The cuff 104 and the device main body 102 are connected by an air tube 108 serving as a connecting tube. According to one or more embodiments of the present invention, the air tube 108 consists of a flexible tube. One end of the air tube 108 is connected to a measurement air system 110 that is provided in the device main body 102. The other end of the air tube 108 is connected to the air bladder 106 of the cuff 104.

The measurement air system 110 supplies air to or discharges air from the air bladder 106 contained in the cuff 104 via air tube 108. The measurement air system 110 includes a pressure sensor 112 that detects the pressure inside the air bladder 106, and a pump 114 and a valve 116 for expanding and contracting the air bladder 106. Supplying air to the air bladder 106 pressurizes the cuff 104, while discharging air from the air bladder 106 depressurizes the cuff 104. The blood pressure measurement device (sphygmomanometer) 100 also includes a central processing unit (CPU) 118, an A/D converter 120, a pump drive circuit 122, and a valve drive circuit 124. The CPU 118 controls the entirety of the blood pressure measurement device (sphygmomanometer) 100. The A/D converter 120, the pump drive circuit 122, and the valve drive circuit 124 are connected to the measurement air system 110.

The pressure sensor 112 detects the internal pressure of the air bladder 106 and inputs a detection signal to the A/D converter 120. The input detection signal is converted to a digital signal by the A/D converter 120, and input to the CPU 118. The CPU 118 executes predetermined processing based on the internal pressure of the air bladder 106 obtained from the pressure sensor 112 and outputs control signals to the pump drive circuit 122 and the valve drive circuit 124 in accordance with the result of the predetermined processing.

The device main body 102 of the blood pressure measurement device (sphygmomanometer) includes a memory unit 126, which stores programs executed by the CPU 118 and results of measurement. That is, the memory unit 126 is constituted by a storage medium. Memory unit 126 may be realized by a single storage medium or more than one storage media. Exemplary storage media include media for storing programs in a non-volatile manner such as CD-ROM (Compact Disc-Read Only Memory), DVD-ROM (Digital Versatile Disk-Read Only Memory), USB (Universal Serial Bus) memory, memory card FD (Flexible Disk), hard disk, magnetic tape, cassette tape, MO (Magnetic Optical Disc), MD (MiniDisc), IC (Integrated Circuit) card (excluding memory card), optical card, mask ROM, EPROM, and EEPROM (Electronically Erasable Programmable Read-Only Memory).

The device main body 102 of the blood pressure measurement device (sphygmomanometer) 100 also includes a display unit 128 and an operation unit 130. The display unit 128 displays the results of measuring blood pressure values, pulse rates, states of rest or unrest, etc. using numerical values, labels, indicia, graphs, and the like in a manner that allows visible confirmation. A liquid crystal panel or the like, for example, may be used as the display unit 128. According to one or more embodiments of the present invention, the operation unit 130 includes a power switch 130a, a measurement switch 130b, a stop switch 130c, and a memory switch 130d.

The device main body 102 of the blood pressure measurement device (sphygmomanometer) 100 also includes a timer 132 and a power supply 134. The timer 132 has a clock function, and the power supply 134 supplies power to the CPU 118. According to one or more embodiments of the present invention, the power supply 134 supplies power to the CPU 118 from an external power supply. According to other embodiments of the present invention, the power supply 134 may be a battery or similar element that supplies power to the CPU 118 without receiving power from an external power supply.

As previously described, the operation unit 130 includes the power switch 130a, the measurement switch 130b, the stop switch 130c, and the memory switch 130d according to one or more embodiments of the present invention. The power switch 130a receives input of an instruction for turning the power supply on or off. The measurement switch 130b receives a measurement start instruction. The stop switch 130c receives a measurement stop instruction. Finally, the memory switch 130d receives an instruction to read out information such as blood pressure recorded in memory unit 126.

The CPU 118 includes a blood pressure calculation section 136 that calculates blood pressure values (a systolic blood pressure value, a diastolic blood pressure value, and/or an average blood pressure value) based on the internal pressure of the air bladder 106 obtained from the pressure sensor 112. The CPU 118 outputs the blood pressure values calculated by the blood pressure calculation section 136 to the display unit 128 to display them as a result of measurement.

The CPU 118 also includes a pulse rate/pulse period change calculation section 138 that calculates the pulse rate and pulse period change of a patient based on a measured pulse period of the patient for a particular phase lasting for a period of time. According to one or more embodiments of the present invention, the measured pulse period may be based on a time period of a detected pulse waveform and/or a change of pulse period. According to one or more embodiments of the present invention, the pulse rate/pulse period change calculation section 138 calculates the pulse rate of the patient in a phase based on the time period of the phase divided by the number of pulses during the phase. According to one or more embodiments of the present invention, the pulse rate/pulse period change calculation section 138 calculates the pulse period change of the patient in a phase based on the difference between the maximum time period of a pulse and the minimum time period of a pulse during the phase. The CPU 118 outputs the pulse rate calculated by the pulse rate/pulse period change calculation section 138 to the display unit 128 to display it as a result of measurement.

The CPU 118 also includes a measurement condition determination section 140 that determines which of a plurality of measurement conditions applies during blood pressure measurement. According to one or more embodiments of the present invention, the plurality of measurement conditions are a plurality of phases, which may include before pressurization of the cuff 104, during pressurization of the cuff 104, and after pressurization of the cuff 104.

The CPU 118 also includes a threshold calculation section 142 that calculates a threshold range for the pulse rate and pulse period change calculated by the pulse rate/pulse period change calculation section 138, with respect to each of the plurality of measurement conditions (i.e., each of the plurality of phases) determined by the measurement condition determination section 140. The CPU 118 outputs the threshold ranges calculated by the threshold calculation section 142 to the memory unit 126 for storage.

The CPU 144 also includes a rest/unrest condition determination section 144 that determines whether the patient is in a rest condition or an unrest condition during blood pressure measurement by comparing present pulse rate and/or pulse period change measurements with the threshold range of past pulse rate and/or pulse period change measurements. If it is determined that the present pulse rate and/or pulse period changes are outside (that is, above or below) the threshold range of past pulse rate and/or pulse period change measurements with respect to any of the plurality of phases, then the rest/unrest condition determination section 144 determines that the patient was in an unrest condition during blood pressure measurement. On the other hand, if it is determined that the present pulse rate and/or pulse period changes are within the threshold range of past pulse rate and/or pulse period change measurements with respect to any of the plurality of phases, then the rest/unrest condition determination section 144 determines that the patient was in a rest condition during blood pressure measurement. The CPU 118 outputs the determination of whether the patient was in an unrest or a rest condition during blood pressure measurement as determined by the rest/unrest condition determination section 144 to the display unit 128 to display it as a result of measurement.

Displaying the blood pressure measurement of the patient on the display unit 128 together with the determination of whether the patient was in an unrest or a rest condition during the blood pressure measurement allows the patient to decide whether the measured blood pressure is reliable.

Figure 2:
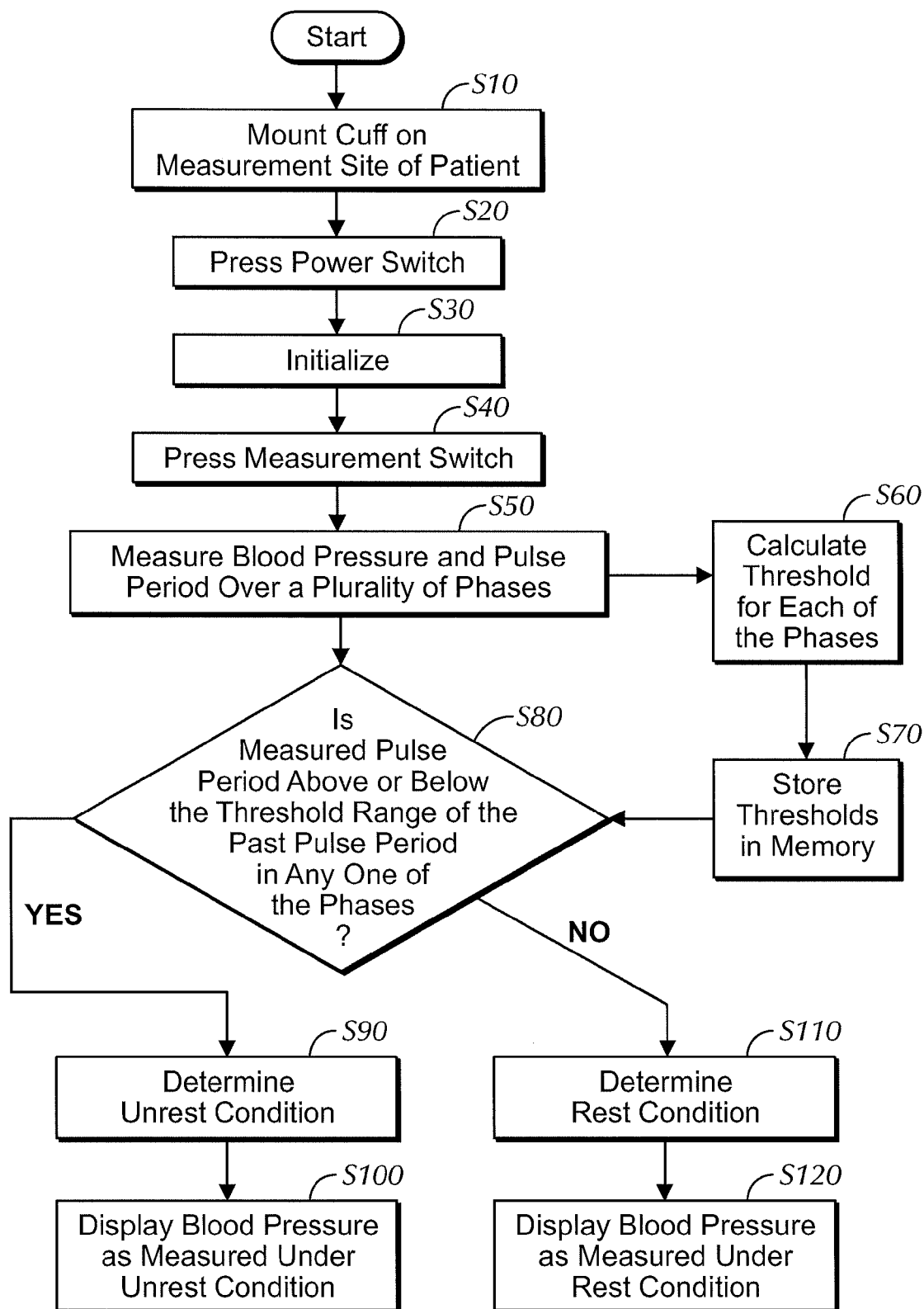
FIG. 2 is a flow chart of processing related to the determination of whether a patient was in a rest condition or an unrest condition during blood pressure measurement according to one or more embodiments of the present invention.

FIG. 2 is a flow chart of processing related to the determination of whether a patient was in a rest condition or an unrest condition during blood pressure measurement according to one or more embodiments of the present invention. In the blood pressure measurement device (sphygmomanometer) 100, this processing is realized by the CPU 118 executing a program stored in the memory unit 126 (or in a recording medium detachable from the device main body 102).

Referring to FIG. 2, in the blood pressure measurement processing, at step S10, the cuff 104 of the blood pressure measurement device (sphygmomanometer) 100 is mounted on a measurement site of the patient.

At step S20, the CPU 118 stands by until the power switch 130a is operated, and advances the processing to step S30 when it is judged that the power switch 130a has been operated.

At step S30, the CPU 118 initializes the blood pressure measurement device (sphygmomanometer) 100. The internal pressure of the air bladder 106 of the cuff 104 is thereby initialized. After initialization, the CPU 118 advances the processing to step S40.

At step S40, the CPU 118 stands by until the measurement switch 130b is operated. When it is judged that the measurement switch 130b has been operated, the CPU 118 advances the processing to step S50.

At step S50, the CPU 118 performs the processing to measure the blood pressure and pulse period of the patient over a plurality of phases. According to one or more embodiments of the present invention, the blood pressure may be a systolic blood pressure value, a diastolic blood pressure value, and/or an average blood pressure value. According to one or more embodiments of the present invention, the measured pulse period may be used to calculate a time period of a detected pulse waveform, that is, the pulse rate, and/or a change of pulse period. According to one or more embodiments of the present invention, the plurality of phases may include before pressurization of the cuff 104, during pressurization of the cuff 104, and after pressurization of the cuff 104. The CPU 118 then advances the processing to step S60.

Figure 3A:
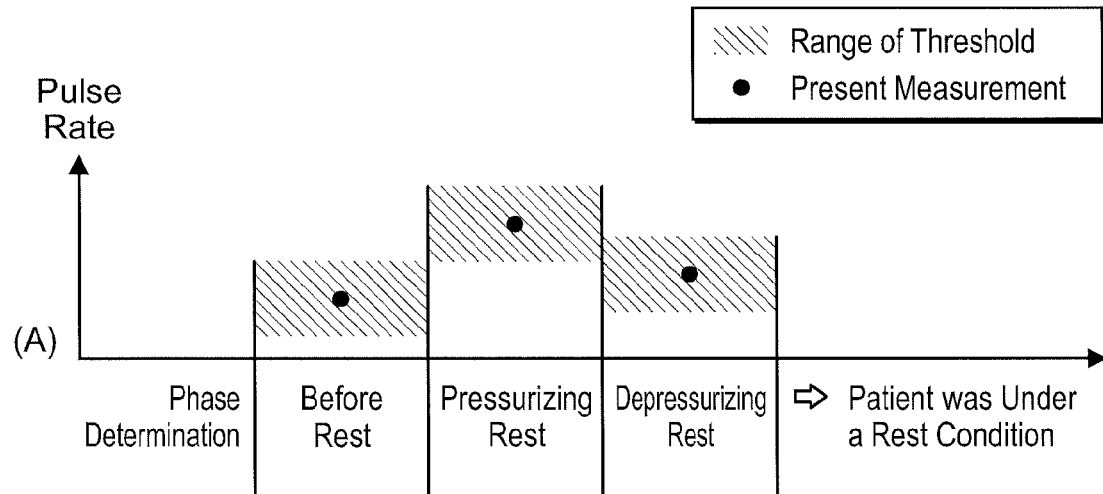
FIGS. 3(A) and 3(B) show a comparison of measured pulse periods with past pulse periods in three phases according to one or more embodiments of the present invention.
Figure 3B:
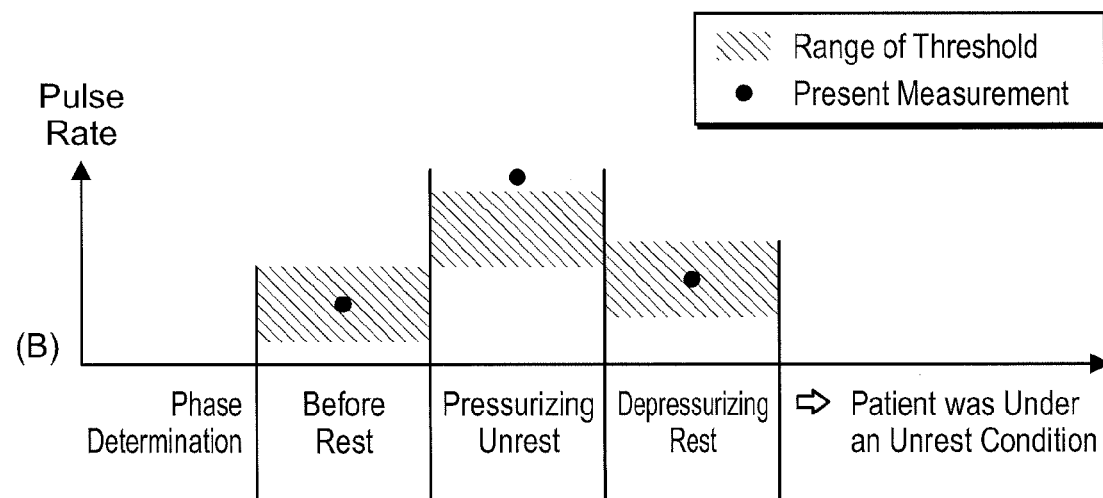

At step S60, the CPU 118 uses the blood pressure and pulse period of the patient over the plurality of phases as measured in step S50 to perform the processing to calculate a threshold value of the pulse rate and pulse period change of the patient with respect to each of the plurality of phases. According to one or more embodiments of the present invention, the threshold value may be a range of threshold values. Examples of threshold value ranges of the pulse rate of a patient with respect to each of a plurality of phases are shown in FIGS. 3A and 3B, which are further described below. The threshold value ranges are shown with shading.

According to one or more embodiments of the present invention, at step S60, the CPU 118 performs the processing to calculate a threshold value range of the pulse rate of the patient with respect to a plurality of phases as further described below. As previously described, the CPU 118 performs the processing to measure the pulse period of the patient over a plurality of phases in step S50. At step S60, the CPU 118 uses the measured pulse period of the patient with respect to a particular phase from step S50 to calculate the pulse rate of the patient. According to one or more embodiments of the present invention, the CPU 118 calculates the pulse rate of the patient with respect to a particular phase by dividing the time length of the phase by the number of pulses that occurred during the phase. As previously described, the plurality of phases may include before pressurization of the cuff 104, during pressurization of the cuff 104, and after pressurization of the cuff 104, according to one or more embodiments of the present invention. As such, at step S60, the CPU 118 calculates the pulse rate of the patient with respect to each of the following phases: a phase that occurs before pressurization of the cuff 104, a phase that occurs during pressurization of the cuff 104, and a phase that occurs after pressurization of the cuff 104, according to one or more embodiments of the present invention.

According to one or more embodiments of the present invention, at step S60, the CPU 118 uses the calculated pulse rates of the patient with respect to each of the plurality of phases to calculate a pulse rate threshold range with respect to each of the plurality of phases. The pulse rate threshold range is delimited by an upper end threshold value and a lower end threshold value. According to one or more embodiments of the present invention, the upper end threshold value and the lower end threshold value for the pulse rate threshold range with respect to each of the plurality of phases may be calculated using Equation 1 and Equation 2, as shown below.

$$\text{Upper end of threshold value} = \text{pulse rate during a phase} \times (1+\alpha) \quad \text{Equation 1.}$$

$$\text{Lower end of threshold value} = \text{pulse rate during a phase} \times (1-\alpha) \quad \text{Equation 2.}$$

Figure 5:
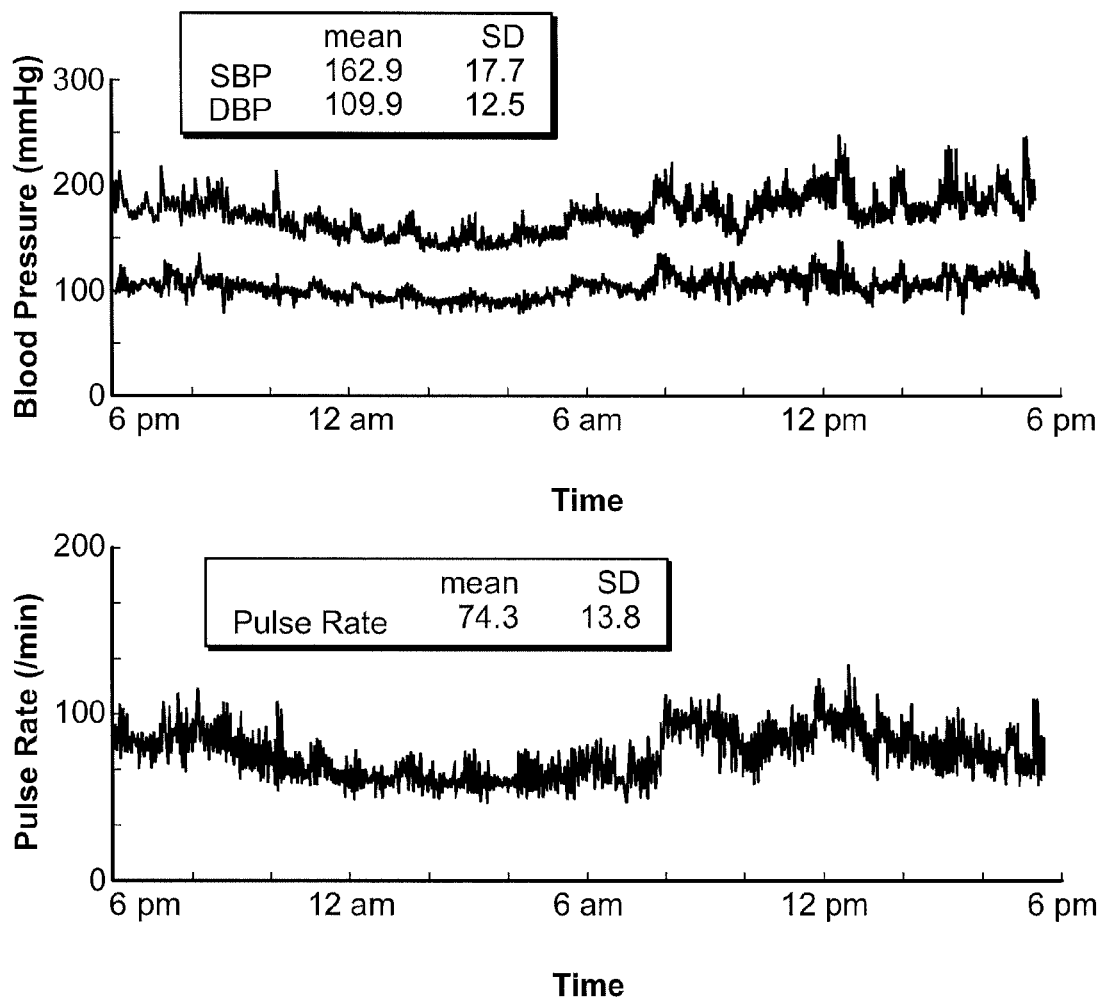
FIG. 5 shows an example of how blood pressure and pulse rate fluctuate depending on the time zone of measurement.

According to one or more embodiments of the present invention, "$\alpha$," as used in Equation 1 and Equation 2, may be set discretionarily in view of a tendency of the blood pressure value and the pulse rate of the patient. Referring now to FIG. 5, an example of how blood pressure and pulse rate fluctuate depending on the time zone of measurement is shown for a particular patient. As shown in FIG. 5, the patient's fluctuation of pulse rate tends be larger during the daytime zone, as compared with the night time zone. Therefore, if the blood pressure measurement was conducted during the daytime time zone, $\alpha$ of Equation 1 and Equation 2 may be set to be 0.15. If the blood pressure measurement was conducted during the night time zone, $\alpha$ of Equation 1 and Equation 2 may be set to be 0.10.

Referring back to FIG. 2, according to one or more embodiments of the present invention, at step S60, the CPU 118 performs the processing to calculate a threshold value range of the pulse period change of the patient with respect to a plurality of phases as further described below. As previously described, the CPU 118 performs the processing to measure the pulse period of the patient over a plurality of phases in step S50. At step S60, the CPU 118 uses the measured pulse period of the patient with respect to a particular phase from step S50 to calculate the pulse period change of the patient. According to one or more embodiments of the present invention, the CPU 118 calculates the pulse period change of the patient with respect to a particular phase based on a difference between a maximum pulse period and a minimum pulse period that occurred during the phase. As previously described, the plurality of phases may include before pressurization of the cuff 104, during pressurization of the cuff 104, and after pressurization of the cuff 104, according to one or more embodiments of the present invention. As such, at step S60, the CPU 118 calculates the pulse period of the patient with respect to each of the following phases: a phase that occurs before pressurization of the cuff 104, a phase that occurs during pressurization of the cuff 104, and a phase that occurs after pressurization of the cuff 104, according to one or more embodiments of the present invention.

According to one or more embodiments of the present invention, at step S60, the CPU 118 uses the calculated pulse period changes of the patient with respect to each of the plurality of phases to calculate a pulse period change threshold range with respect to each of the plurality of phases. The pulse period change threshold range is delimited by an upper end threshold value and a lower end threshold value. According to one or more embodiments of the present invention, the upper end threshold value and the lower end threshold value for the pulse period change threshold range with respect to each of the plurality of phases may be calculated using Equation 3 and Equation 4, as shown below.

$$\text{Upper end of threshold value} = \text{pulse period change during a phase} \times (1+\alpha) \quad \text{Equation 3.}$$

$$\text{Lower end of threshold value} = \text{pulse period change during a phase} \times (1-\alpha) \quad \text{Equation 4.}$$

According to one or more embodiments of the present invention, "$\alpha$," as used in Equation 3 and Equation 4, may be set discretionarily in view of a tendency of the blood pressure value and the pulse rate of the patient. Referring now to FIG. 5, an example of how blood pressure and pulse rate fluctuate depending on the time zone of measurement is shown for a particular patient. As shown in FIG. 5, the patient's fluctuation of pulse rate tends be larger during the daytime zone, as compared with night time zone. Therefore, if the blood pressure measurement was conducted during the daytime time zone, $\alpha$ of Equation 3 and Equation 4 may be set to be 0.15. If the blood pressure measurement was conducted during the night time zone, $\alpha$ of Equation 3 and Equation 4 may be set to be 0.10.

According to one or more embodiments of the present invention, the pulse period may be measured a plurality of times at step S50 so that, at step S60, an average of the plurality of pulse period measurements may be used to calculate the threshold value ranges with respect to each of the plurality of phases. Using an average of the plurality of pulse period measurements in accordance with one or more embodiments of the present invention may result in more reliable threshold value ranges. After the CPU 118 performs the processing to calculate the pulse rate and/or pulse period change threshold value ranges with respect to each of the plurality of phases, the CPU 118 advances the processing to step S70.

At step S70, the CPU 118 stores in the memory unit 126 the threshold value ranges with respect to each of the plurality of phases, as calculated at step S60. After step S70, the CPU 118 advances the processing to step S80.

At step S80, the CPU 118 performs the processing to determine whether the presently measured pulse rate or the presently measured pulse period change as based on the presently measured pulse period is within or beyond the threshold value range of the past-measured pulse rate or the past-measured pulse period change as based on the past-measured pulse period (or an average of past-measure pulsed periods) in at least one of the corresponding plurality of phases. If the presently measured pulse rate or the presently measured pulse period change is beyond the threshold value range of the past-measured pulse rate or the past-measured pulse period change in at least one of the corresponding plurality of phases, then the CPU 118 advances the processing to step S90 and determines that the patient was in an unrest condition during blood pressure measurement. After step S90, the CPU 118 advances the processing to step S100 to display on the display unit 128 the presently measured blood pressure was measured when the patient was in an unrest condition. On the other hand, if the presently measured pulse rate or the presently measured pulse period change is within the threshold value range of the past-measured pulse rate or the past-measured pulse period change in at least one of the corresponding plurality of phases, then the CPU 118 advances the processing to step S110 and determines that the patient was in a rest condition during blood pressure measurement. After step S110, the CPU 118 advances the processing to step S120 to display on the display unit 128 the presently measured blood pressure was measured when the patient was in a rest condition.

FIG. 3 shows an example of a comparison of measured pulse periods with past pulse periods in three phases according to one or more embodiments of the present invention. As shown in FIG. 3(A), if the presently measured pulse period (which as shown here, was used to calculate the pulse rate) is within the threshold value range in all of the plurality of phases (e.g., the phase that occurs before pressurization of the cuff 104, the phase that occurs during pressurization of the cuff 104, and the phase that occurs after pressurization of the cuff 104), then it is determined that the patient was under a rest condition during blood pressure measurement, and the blood pressure is displayed as measured under the rest condition. On the other hand, if the presently measured pulse period is beyond or below the threshold value range in any one of the plurality of phases as shown in FIG. 3 (B), then it is determined that the patient was under an unrest condition during blood pressure measurement, and the blood pressure is displayed as measured under the unrest condition.

Figure 4A:
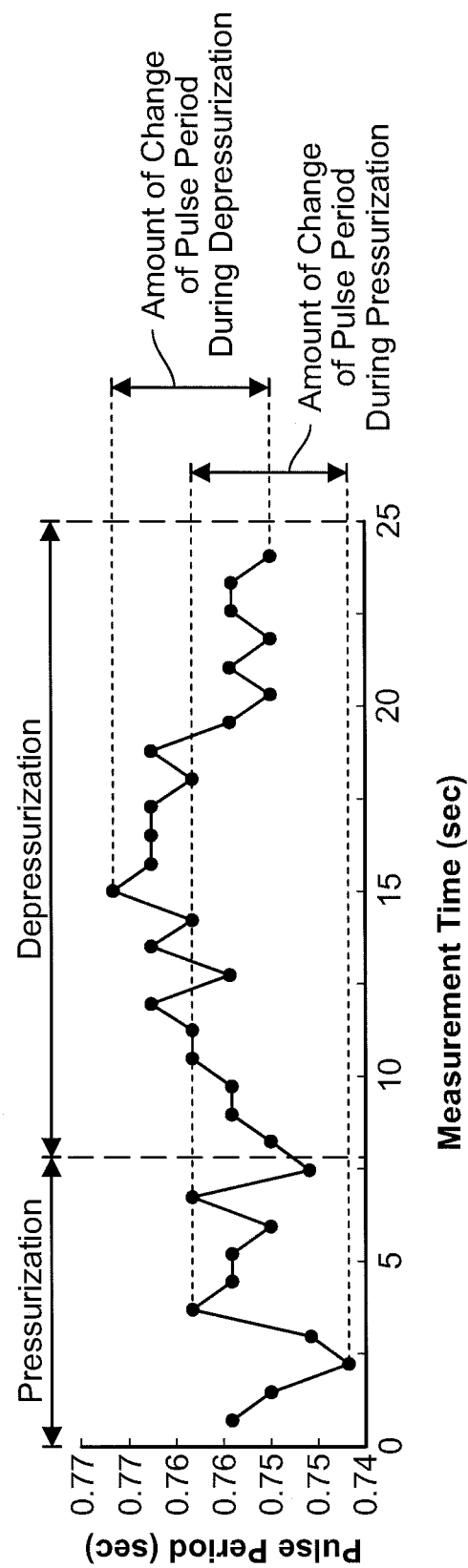

FIGS. 4(A) and 4(B) show measurement data of pulse periods during pressurization and depressurization phases of the cuff of the blood pressure measurement device (sphygmomanometer) according to one or more embodiments of the present invention.

As shown in FIGS. 4(A) and 4(B), the total time lapsed during the pressurization phase of blood pressure measurement is 7.491667 seconds. As also shown in FIGS. 4(A) and 4(B), a pulse was measured 10 times during the pressurization phase of blood pressure measurement. As such, in this example, the pulse period in the pressurization phase of blood pressure measurement is 7.491667 seconds/10 times=0.7491667 sec. Therefore, the pulse rate during the pressurization phase is calculated by: 60 sec/0.7491667 sec=80.01.

As further shown in FIGS. 4(A) and 4(B) the total time lapsed during the depressurization phase of blood pressure measurement is 24.16167 seconds−7.491667 seconds=16.67 seconds. As also shown in FIGS. 4(A) and 4(B), a pulse was measured 22 times during the depressurization phase of blood pressure measurement. As such, in this example, the pulse period in the depressurization phase of blood pressure measurement is 16.67 seconds/22 times=0.757 sec. Therefore, the pulse rate during the depressurization phase is calculated by: 60 sec/0.757 sec=79.26.

In view of the above, the threshold range of the pulse rate calculated from past measurements during the pressurization phase as shown in FIGS. 4(A) and 4(B) may be calculated as follows, based on Equation 1 and Equation 2:

Upper end of threshold value of pulse rate during pressurization phase is 80.01×(1+0.15)=92.01.

Lower end of threshold value of pulse rate during pressurization phase is 80.01×(1−0.15)=68.01.

As shown in this example, "α" of Equation 1 and Equation 2 has been set to 0.15 to account for the tendency of the blood pressure value and the pulse rate of the patient. With respect to this example, if the presently measured pulse rate of the patient during the pressurization phase is measured to be beyond 92.01 or below 68.01, then it is determined that the presently measured pulse rate was conducted when the patient was in an unrest condition. On the other hand, if the presently measured pulse rate of the patient during the pressurization phase is measured to be within the threshold range of 68.01 to 92.01, then it is determined that the presently measured pulse rate was conducted when the patient was in a rest condition.

Further, the threshold range of the pulse rate calculated from past measurements during the depressurization phase as shown in FIGS. 4(A) and 4(B) may be calculated as follows, based on Equation 1 and Equation 2:

Upper end of threshold value of pulse rate during depressurization phase is 79.26×(1+0.15)=91.15.

Lower end of threshold value of pulse rate during depressurization phase is 79.26×(1−0.15)=67.37.

As shown in this example, "α" of Equation 1 and Equation 2 has been set to 0.15 to account for the tendency of the blood pressure value and the pulse rate of the patient. With respect to this example, if the presently measured pulse rate of the patient during the depressurization phase is measured to be beyond 91.15 or below 67.37, then it is determined that the presently measured pulse rate was conducted when the patient was in an unrest condition. On the other hand, if the presently measured pulse rate of the patient during the depressurization phase is measured to be within the threshold range of 67.37 to 91.15, then it is determined that the presently measured pulse rate was conducted when the patient was in a rest condition.

Still referring to FIGS. 4(A) and 4(B), the maximum pulse period during the pressurization phase is 0.758333 sec. The minimum pulse period during the pressurization phase is 0.741667 sec. As such, in this example, the pulse period change in the pressurization phase is 0.758333 sec. (max)–0.741667 sec. (min)=0.01666 sec.

On the other hand, the maximum pulse period during the depressurization phase is 0.766667 sec. The minimum pulse period during the depressurization phase is 0.75 sec. As such, in this example, the pulse period change in the depressurization phase is 0.766667 sec. (max)–0.75 sec. (min)=0.01667 sec.

In view of the above, the threshold range of the pulse period change calculated from past measurements during the pressurization phase as shown in FIGS. 4(A) and 4(B) may be calculated as follows, based on Equation 3 and Equation 4:

Upper end of threshold value of pulse period change during pressurization phase is 0.01666 sec.×(1+0.15)=0.019159 sec.

Lower end of threshold value of pulse period change during pressurization phase is 0.01607 sec.×(1−0.15)=0.014169 sec.

As shown in this example, "α" of Equation 3 and Equation 4 has been set to 0.15 to account for the tendency of the blood pressure value and the pulse rate of the patient. With respect to this example, if the presently measured pulse change period of the patient during the pressurization phase is measured to be beyond 0.019159 sec. or below 0.014169 sec., then it is determined that the presently measured pulse change period was conducted when the patient was in an unrest condition. On the other hand, if the presently measured pulse change period of the patient during the pressurization phase is measured to be within the threshold range of 0.014169 sec. to 0.019159 sec., then it is determined that the presently measured pulse change period was conducted when the patient was in a rest condition.

Further, the threshold range of the pulse period change calculated from past measurements during the depressurization phase as shown in FIGS. 4(A) and 4(B) may be calculated as follows, based on Equation 3 and Equation 4:

Upper end of threshold value of pulse period change during depressurization phase is 0.01667 sec.×(1+0.15)=0.0191705 sec.

Lower end of threshold value of pulse period change during depressurization phase is 0.01667 sec.×(1−0.15)=0.0141695 sec.

As shown in this example, "α" of Equation 3 and Equation 4 has been set to 0.15 to account for the tendency of the blood pressure value and the pulse rate of the patient. With respect to this example, if the presently measured pulse change period of the patient during the depressurization phase is measured to be beyond 0.0191705 sec. or below 0.0141695 sec., then it is determined that the presently measured pulse change period was conducted when the patient was in an unrest condition. On the other hand, if the presently measured pulse change period of the patient during the depressurization phase is measured to be within the threshold range of 0.0141695 sec. to 0.0191705 sec., then it is determined that the presently measured pulse change period was conducted when the patient was in a rest condition.

Therefore, the blood pressure measurement device (sphygmomanometer) 100 according to one or more embodiments of the present invention accurately determines whether a patient was in a rest condition during blood pressure measurement while taking into account (or regardless of) a change of the pulse period that may be caused by use of a cuff of the blood pressure measurement device.

Figure 6:
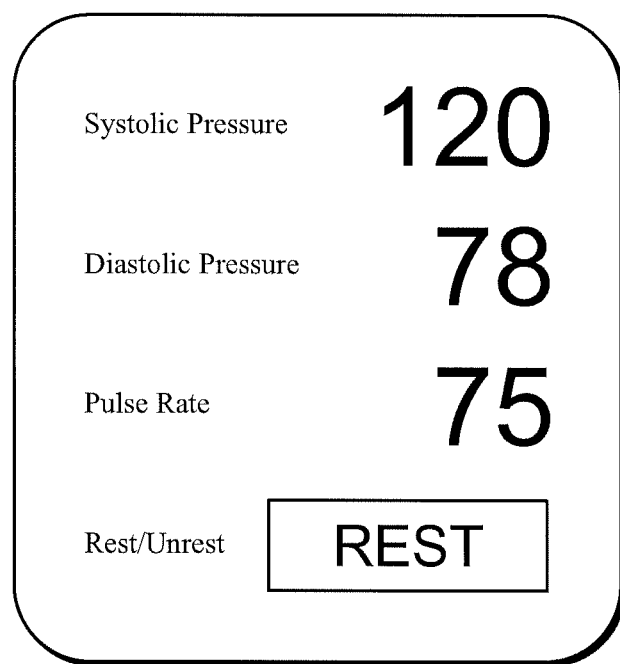
FIG. 6 is an example display of data on a display unit of a blood pressure measurement device (sphygmomanometer) according to one or more embodiments of the present invention.

FIG. 6 is an example display of data on a display unit of a blood pressure measurement device (sphygmomanometer) according to one or more embodiments of the present invention. As shown in FIG. 6, the example display may show the blood pressure (systolic blood pressure and diastolic blood pressure) and the pulse rate of a patient together with a determination of whether the patient was in a rest or an unrest condition during blood pressure measurement, according to one or more embodiments of the present invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A method of determining a rest or an unrest condition of a patient during measurement of blood pressure of the patient, the method comprising:
   providing a cuff of a blood pressure measurement device that is configured to be wrapped around a measurement site of the patient, and pressurizing the cuff;
   measuring the blood pressure and a pulse period of the patient during and before depressurization of the cuff;
   calculating a threshold value range of the pulse period measured during and before depressurization of the cuff based on data of a pulse period measured in a past measurement of the patient and stored in a memory of the blood pressure measurement device,
      wherein an upper end of the threshold value range comprises a product of: the pulse period measured either during or before depressurization of the cuff; and a discretionary constant plus one, and
      wherein a lower end of the threshold value range comprises a product of: the pulse period measured either during or before depressurization of the cuff; and one minus the discretionary constant;
   determining whether the pulse period of the patient measured during and before depressurization of the cuff is within the threshold value range of the pulse period stored in the memory;
   if the pulse period measured during and before depressurization is determined to be within the threshold value range of the pulse period stored in the memory both during and before depressurization, displaying on a display of the blood pressure measurement device that the blood pressure was measured when the patient was in the rest condition, and
   if the pulse period measured during and before depressurization is determined not to be within the threshold value range of the pulse period stored in the memory either during or before depressurization, displaying on the display of the blood pressure measurement device that the blood pressure was measured when the patient was in the unrest condition.

2. The method of measuring the blood pressure of the patient according to claim 1, further comprising adjusting the threshold value range of the pulse period stored in the memory depending on a condition of at least one of the blood pressure measurement and the pulse period measurement.

3. The method of measuring the blood pressure of the patient according to claim 1, further comprising determining whether the patient was in the rest condition or the unrest condition during blood pressure measurement by examining both a pulse rate and a pulse period change of the patient, and if at least one of the pulse rate and the pulse period change is found to be different from a pulse rate and a pulse period change of past measurement of the patient by more than a threshold value, determining that the blood pressure was measured when the patient was in the unrest condition.

4. The method of measuring the blood pressure of the patient according to claim 3,
   wherein the pulse rate and the pulse period change of the patient is based on the measured pulse period of the patient, and
   wherein the pulse rate and the pulse period change of past measurement of the patient is based on the pulse period measured in the past measurement of the patient.

5. A blood pressure measurement device that determines a rest or an unrest condition of a patient, the device comprising:
   a cuff for mounting on a measurement site of the patient, wherein the cuff is configured to be pressurized and depressurized to measure a blood pressure and a pulse period of the patient;
   means for measuring the blood pressure and the pulse period of the patient during and before depressurization of the cuff;
   a memory that stores data of a pulse period measured in a past measurement of the patient by the measuring means;
   a threshold calculation section that calculates a threshold value of the pulse period measured during and before depressurization of the cuff based on data of the pulse period measured in the past measurement of the patient, wherein the threshold value is a threshold value range,
      wherein if the pulse period was measured during depressurization of the cuff,
         an upper end of the threshold value range comprises a product of: the pulse period measured during depressurization of the cuff; and a discretionary constant plus one, and
         a lower end of the threshold value range comprises a product of: the pulse period measured during depressurization of the cuff; and one minus the discretionary constant, and
      wherein if the pulse period was measured before depressurization of the cuff,
         an upper end of the threshold value range comprises a product of: the pulse period measured before depressurization of the cuff; and the discretionary constant plus one, and
         a lower end of the threshold value range comprises a product of: the pulse period measured during depressurization of the cuff; and one minus the discretionary constant;
   a rest/unrest condition determination section that determines whether the patient was in a rest condition or an unrest condition during blood pressure measurement by comparing the pulse period measured during and before depressurization of the cuff with the threshold value based on data of the pulse period measured in the past measurement of the patient; and
   a display unit that displays the measured blood pressure and whether the blood pressure was measured during the rest condition or the unrest condition of the patient.

6. The blood pressure measurement device according to claim 5, wherein the threshold calculation section adjusts the threshold value depending on a measurement condition of the patient.

7. The blood pressure measurement device according to claim 5,
   wherein the rest/unrest condition determination section determines whether the patient was in the rest condition or the unrest condition during blood pressure measurement by examining both a pulse rate of the patient measured during and before depressurization of the cuff and a pulse period change of the patient measured during and before depressurization of the cuff, and if at least one of the pulse rate of the patient measured during and before depressurization of the cuff and the pulse period change of the patient measured during and before depressurization of the cuff is found to be different from a pulse rate of past measurement of the patient and a pulse period change of past measurement of the patient by more than a corresponding threshold value, the patient is determined to have been in the unrest condition during blood pressure measurement,
   wherein the pulse rate of the patient measured during and before depressurization of the cuff and the pulse period change of the patient measured during and before depressurization of the cuff are based on the pulse period of the patient measured during and before depressurization of the cuff, and
   wherein the pulse rate of past measurement of the patient and the pulse period change of past measurement of the patient are based on the pulse period measured in the past measurement of the patient.

8. A blood pressure measurement device that determines a rest or an unrest condition of a patient, the device comprising:
   a cuff for mounting on a measurement site of the patient, wherein the cuff comprises an air bladder and is configured to be pressurized and depressurized to measure a blood pressure and a pulse period of the patient;
   a measurement air system comprising a pressure sensor, a pump, and a valve;
   an air tube that connects the air bladder of the cuff to the measurement air system;
   a blood pressure calculation section that calculates a blood pressure of the patient based on an internal pressure of the air bladder as detected by the pressure sensor;
   a heart rate/pulse period change calculation section that calculates a pulse rate of the patient during and before depressurization of the cuff and a pulse period change of the patient during and before depressurization of the cuff based on the measured pulse period of the patient;
   a memory that stores data of a pulse period measured in a past measurement of the patient;
   a threshold calculation section that calculates a threshold value of at least one of the pulse rate of the patient calculated during and before depressurization of the cuff and the pulse period change of the patient calculated during and before depressurization of the cuff based on data of the pulse period measured in the past measurement of the patient,
      wherein the threshold value is a threshold value range,
      wherein, with respect to the threshold value of the pulse rate or the pulse period change of the patient calculated during depressurization of the cuff,
         an upper end of the threshold value range comprises a product of: the pulse rate or the pulse period change calculated during depressurization of the cuff; and a discretionary constant plus one, and
         a lower end of the threshold value range comprises a product of: the pulse rate or the pulse period change calculated during depressurization of the cuff; and one minus the discretionary constant,
      wherein, with respect to the threshold value of the pulse rate or the pulse period change of the patient calculated before depressurization of the cuff,
         an upper end of the threshold value range comprises a product of: the pulse rate or the pulse period change calculated before depressurization of the cuff; and the discretionary constant plus one, and a lower end of the threshold value range comprises a product of: the pulse rate or the pulse period change calculated before depressurization of the cuff; and one minus the discretionary constant;

a rest/unrest condition determination section that determines whether the patient was in a rest condition or an unrest condition during blood pressure measurement by comparing at least one of the pulse rate of the patient calculated during and before depressurization of the cuff and the pulse period change of the patient calculated during and before depressurization of the cuff with the threshold value based on data of the pulse period measured in the past measurement of the patient; and a display unit that displays the measured blood pressure and whether the blood pressure was measured during the rest condition or the unrest condition of the patient.

9. The blood pressure measurement device according to claim 8, wherein the threshold calculation section adjusts the threshold value depending on a measurement condition of the patient.

10. The blood pressure measurement device according to claim 8, wherein the rest/unrest condition determination section determines whether the patient was in the rest condition or the unrest condition during blood pressure measurement by examining both the pulse rate of the patient calculated during and before depressurization of the cuff and the pulse period change of the patient calculated during and before depressurization of the cuff, and if at least one of the pulse rate of the patient calculated during and before depressurization of the cuff and the pulse period change of the patient calculated during and before depressurization of the cuff is found to be different from a pulse rate of past measurement of the patient and a pulse period change of past measurement of the by more than a corresponding threshold value, the patient is determined to have been in the unrest condition during blood pressure measurement, and wherein the pulse rate of past measurement of the patient and the pulse period change of past measurement of the patient are based on the pulse period measured in the past measurement of the patient.

\* \* \* \* \*